United States Patent [19]

Schäfer

[11] 4,456,596

[45] Jun. 26, 1984

[54] WOUND HEALING GLYCOSIDE COMPOSITIONS

[76] Inventor: Rolf Schäfer, Gravenmattstrasse 37, 4133 Pratteln BL, Switzerland

[21] Appl. No.: 253,872

[22] Filed: Apr. 13, 1981

[51] Int. Cl.³ .................... A61K 31/705; C07J 17/00
[52] U.S. Cl. .................................. 424/180; 424/177; 424/182; 536/5
[58] Field of Search .................... 536/5, 17.9, 53, 123; 424/182, 180

[56] References Cited

U.S. PATENT DOCUMENTS 3,579,499 5/1971 Clarkson ................................ 536/5
4,296,233 10/1981 Enomoto et al. ....................... 536/5

*Primary Examiner*—Johnnie R. Brown

[57] ABSTRACT

Compositions which stimulate tissue regeneration and whose active components are substances present in mammalian tissues and fluids are described. The active substances are a polypeptide consisting of 52 amino acids and having a molecular weight of about 5800, a glycosteroid and a glycosphingolipid. Compositions which contain the active ingredients accelerate wound healing when applied in the nano- to microgram ranges. Means for recovering the substances from mammalian materials in concentrated form by biochemical parting methods are also described.

16 Claims, No Drawings

WOUND HEALING GLYCOSIDE COMPOSITIONS

BACKGROUND OF THE INVENTION (a) Field of the Invention

This invention relates to materials in mammalian tissues or fluids which accelerate wound healing.

(b) State of the Art

The use of topically or systemically applied drugs for accelerated healing processes of physically, chemically or physiologically induced tissue lesion, such as burns, surgery or ulcers, is described in the medicinal literature. For example, there are reports on anabolic steroids, vitamin A, vitamin K, zinc compounds, silver compounds or serum factors, e.g. factor XIII in blood coagulation, or high molecular compounds such as collagen or cartilage which all accelerate the healing process of tissue injuries. There are also reports on the successful treatment of tissue injuries with crude extracts from aloe or with low molecular weight extracts from mammalian organs. Such plant or animal extracts contain complex mixtures of poorly defined material with low levels of the active ingredients and high levels of inorganic salts.

The present invention provides three low molecular weight compounds from crude extracts of mammalian organs, blood, serum, or plasma which all accelerate the healing process of mammalian and human tissue injuries. The compounds can be isolated in relatively concentrated and pure form and have been substantially identified.

SUMMARY OF THE INVENTION

This invention relates to compositions containing substances which are present in biological material and accelerate regeneration of internal and external tissue lesions.

The first substance is a polypeptide consisting of 52 amino acids and having a molecular weight of 5800. This material is present in the pancreas, blood, serum and plasma of mammals and stimulates growth of the cell framework during early stages of wound healing.

The second substance is a glycosteroid having the structure:

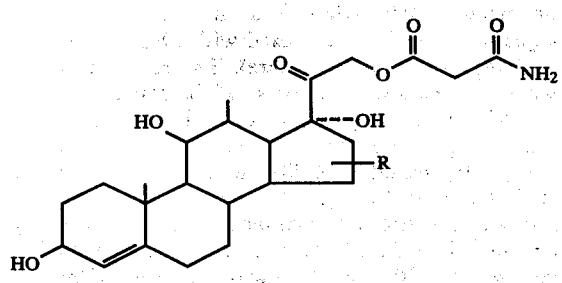

wherein R is an oligosaccharide which contains five sugar groups and the hydroxyl groups of the steroid may be acetylated. The material can be isolated from mammalian tissues and fluids and promotes proliferation of epithelium cells in the final phase of wound healing.

The final material is a glycosphingolipid of the structure:

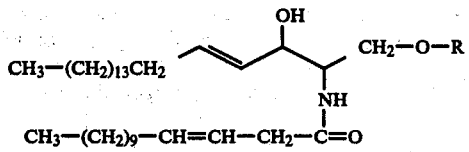

wherein R is an oligosaccharide having five sugar groups. This material can be isolated from mammalian tissues and fluids and promotes fibroblast formation in wounds after capillarization and vascularization begins.

DETAILED DESCRIPTION OF THE INVENTION

The present invention provides compositions containing an active material which is isolated from mammalian tissues or fluids and which stimulate wound healing. The compositions comprise a carrier and at least one of three active materials of mammalian origin.

The first substance is a polypeptide consisting of 52 amino acids and having a molecular weight of 5800. This material is present in the pancreas, blood, serum and plasma of mammals and stimulates growth of the cell framework during early stages of wound healing.

The polypeptide can be isolated from the pancreas, plasma, blood and serum of mammals. The material is particularly concentrated in the pancreas. Mammals from which the material can be isolated are swine, horses, sheep, humans and beef.

Isolation of the material can be effected by fractionating the starting material to isolate a precipitate containing the alpha and beta globulins. The precipitate is then treated to remove impurities particularly proteins, as by extractions and precipitation. The material dissolved in acid may then be further isolated by means of column chromatography. An exemplary detailed means for isolation of the polypeptide is set forth hereinbelow.

The polypeptide stimulates wound healing specifically proliferation of epitheleum cells and fibroblasts is accelerated during early stages of wound healing. The polypeptide is optimally effective at 25 ng/ml of topically applied compositions. At higher levels the marginal increase in healing rate is insignificant.

The composition of the invention comprises any physiologically acceptable carrier suitable for topical use plus the polypeptide. Examples of suitable carriers include carboxymethyl cellulose, oil-in-water emulsions, water-in-oil emulsions, aqueous inorganic salt solutions or other conventional liquid, gel or ointment carrier materials.

The second active substance for use in compositions of the invention is a glycosteroid having the structure:

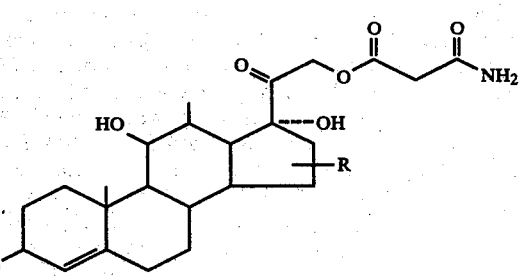

wherein R is an oligosaccharide which contains five sugar groups and the hydroxyl groups of the steroid may be acetylated. The material can be isolated from mammalian tissues and fluids and promotes proliferation of epithelium cells in the final phase of wound healing.

The final material is a glycosphingolipid of the structure:

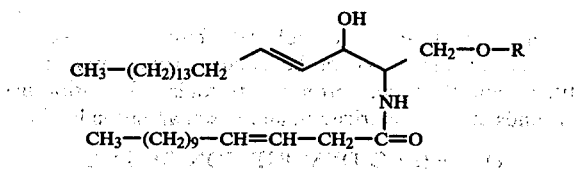

wherein R is an oligosaccharide having five sugars groups. This material can be isolated from mammalian tissues and fluids and promotes fibroblast formation in wounds after capillarization and vascularization begins.

These second and third materials can be isolated from mammalian organs such as heart, lung, muscle and spleen or mammalian fluids, such as blood, plasma or serum. Relatively higher concentrations of these materials are generally found in the organs. The mammals which have been found to produce these materials are humans, swine, horses, sheep and beef.

Isolation of these materials can be accomplished by isolating an essentially protein-free fraction of the starting material having a molecular weight below 10,000, using a combination of techniques such as ultrafiltration, centrifugation and the like. Removal of the inorganic salts from the material may then be effected as by binding the active materials to active carbon. The materials can than be further isolated and parted from each other chromatographically. Details of exemplary means for isolating these materials are set forth below.

The maximum acceleration of wound healing is achieved when the glycosphingolipid is applied at a rate of 50 µg/ml of composition. The glycosteroid is maximally effective when applied at rates of 10 µg/ml of composition. Optimal rates of application are 5 µg/ml of the glycosphingolipid and 1 µg/ml of the glycosteroid. Carriers of the type suitable for use with the polypeptide may be employed with the latter materials as well.

The following examples are illustrative of the invention.

EXAMPLE 1

(a) Isolation of the Polypeptide

Isolation of the wound healing polypeptide useful in the present invention was effected as follows:

3500 liters beef plasma containing 5% protein (w/v) (EDTA-, heparin- or citrate-stabilized) were fractionated as follows: 350 l ethanol were added to 3500 l of the plasma solution at pH 7.2±0.3 and mixed for 10 minutes with a metal blade rotating at 500 rpm. The mixture was stored for 12 hours at $-3°$ C.±0.5° C. and the precipitated protein was removed by centrifugation at 8000×g for 20 minutes. 315 l ethanol were then added to the clear supernatant and mixed as described above. Then the pH of the solution was adjusted with 10N HCl to 5.85±0.05. This mixture was stored for 12 hours at $-5°$ C.±1° C. and the precipitated protein was removed by centrifugation as described above. 730 liters ethanol were again added to the clear supernatant and mixed as described above. The pH of the solution was kept at 5.85. The mixture was stored for 12 hours at $-9±2°$ C. and the precipitated protein was collected by centrifugation as described above. The clear supernatant was discarded. The precipitate containing alpha and beta globulins (8.5 kg) was homogenized with 350 liters 75% ethanol-0.20M HCl at 4±1° C. for 15 minutes. Thereafter the homogenate was centrifuged for 5 minutes at 10,000×g. The resulting sediment was extracted again with ethanol-hydrochloride solution using the same conditions described above.

The combined supernatants were adjusted to pH 8.5±0.5 with 10 N NaOH, mixed with 4 volumes of acetone-ethanol (5/3, v/v) and cooled to $-20°±2°$ C. After 14 hours the supernatant was decanted and the precipitate (acetone powder) was dried under vacuum (1-10 mm Hg) at room temperature. The yield was 150 g.

The precipitate was extracted three times at room temperature for 4 hours with 1 liter of a 3% acetic acid. The combined supernatants were put on a molecular sieve, i.e., a Pharmacia sectional column KS 370 (total volume 65 liters) packed with Sephadex G75 (Pharmacia), equilibrated at 3% acetic acid and chromatographed at room temperature (rate of flow: 4 liters/hour, fractions: 2 liters). Three peaks eluted after 20, 50 and 70 liters of solvent. They were detected with a 200 nm monitor. The peak which eluted after 50 liters of the solvent was collected and the solvent was evaporated under vacuum at 40° C. and 10-20 mm Hg and yielded 1 g of material. The peak material was dissolved in 0.3 liter of 6% acetic acid, put on a molecular sieve, i.e., 10-liter Sephadex G50 column (Pharmacia) equilibrated in 6% acetic acid and chromatographed at room temperature (rate of flow: 1.5 liters/hour, fractions: 0.5 liter). Six peaks eluted from this column. The last peak fraction, which eluted after 11 liters of solvent, was collected and the solvent was evaporated under vacuum at 40° C. and 10-20 mg Hg and yielded 160 mg of material. This material was dissolved in 10 mM phosphate buffer at pH 7 and put on a 50 ml carboxymethyl cellulose ion exchanger column (Whatman) equilibrated in 10 mM phosphate buffer. Five fractions were eluted with a linear NaCl gradient (10 mM-150 mM) at room temperature. 10 mg of material, which eluted at 125 mM NaCl, was pure polypeptide of the invention.

It is very important that during the extraction procedure temperature and pH be kept in the above-described limits. Variations result in decreased recovery of the polypeptide of the invention.

Where the starting material is serum the first ethanol precipitation (9% ethanol) is omitted. The serum is adjusted to pH 5.85 and mixed with 19% ethanol (step 2 of the extraction procedure). The subsequent steps were than as described above. If the starting material was whole blood, the blood was clotted for 6 hours at room temperature and the serum was separated from the clot by decantation. The serum was then fractionated as described above. The polypeptide of the invention was also isolated from blood, plasma or serum of human, swine, horse and sheep. The recovery of the polypeptide of the invention was in all cases of the same order of magnitude based on the amount of starting material.

In case of pancreas from swine, horses, sheep and beef 1000 Kg of glands were homogenized mechanically in the presence of 2500 l of a 0.8% NaCl solution of 4° C. Cellular debris was removed by centrifugation for 15 minutes at 10,000×g. The clear supernatant was fractionated as described in Example 1. Based on the amount of protein in the starting material the recovery of the polypeptide of the invention was 28 to 32 times higher in beef pancreas as compared to beef plasma. The recovery of the polypeptide of the invention from the pancreas of swine, horses, sheep and beef was in all cases of the same order of magnitude.

(b) Biological Activity of the Polypeptide

The cell-proliferating activity of the materials produced during the isolation procedure were analyzed. Cell-proliferating activity was tested in vitro on primary human fibroblasts and epithelial cells. The cells which grew as monolayers in Petri dishes from Falcon were synchronized in the confluent stage by serum removal for 18 hours. Thereafter $^{14}C$-leucine incorporation into protein and the $^3H$-thymidine incorporation into DNA of the cells were measured as follows:

After synchronization, vacuum dried aliquots of every fraction from the columns were dissolved in water with 0.8% NaCl and added with a pipette to the cell cultures for 10 hours. The amount of the tested protein of the aliquots which were added to each cell culture flask was 100 µg of the acetone powder, 1–10 µg of the acetic acid extract, 0.2–1 µg of the Sephadex G25 eluates, 10–50 ng of the Sephadex G50 eluates and 2–55 ng of the CM-cellulose extracts per ml of medium in the cell cultures. Thereafter a 5-hour pulse of $^{14}C$-leucine or $^3H$-thymidine (20 µM, 1 µCi/ml medium for $3 \times 10^6$ cells in a Petri dish of 5 cm diameter) was administered. The control cultures were not treated with the polypeptide. One unit of polypeptide of the invention was defined as that amount which in 1 ml cell culture medium produced maximum stimulation (350%) of the thymidine incorporation into DNA in comparison with the control. Table I and II summarize the results of the isolation procedure and of the biological tests.

TABLE 1

| Fraction | Activity (Units/mg) | Concentration | Yield | Total |
|---|---|---|---|---|
| Acetone powder | 6.5 | — | 100 | 150 g |
| Acetic Acid extract | 65 | 10× | 95 | 14 g |
| Sephadex G 75 column eluate | 650 | 100× | 80 | 1 g |
| Sephadex G 50 Column eluate | 4000 | 600× | 80 | 160 mg |
| CM-cellulose column eluate | 40000 | 6000× | 50 | 8 mg |

TABLE II

| H—thymidine incorporation in primary human fibroblasts | |
|---|---|
| Pure Polypeptide (nanogram/ml medium) | Percent Stimulation relative to control |
| 2.5 | 150 |
| 7.5 | 200 |
| 10 | 300 |
| 25 | 350 |

In vivo cell-proliferating activity was also measured in punch and burn wounds on guinea pigs. In these tests, anesthetized guinea pigs were shaved and depilated on both sides of the neck. The shaved area was 25 cm² on each side. In case of punch wounds, two punches with a diameter of 1.5 cm were placed with a knife on each side of the neck. The wounds were 2 mm deep. In case of burn wounds the animals were treated for 20 seconds with a cylindrical copper block (1.5 cm in diameter, 50 g by weight) which was heated to 250° C. Two burns were placed on each side of the shaved neck.

25 animals with punch wounds and 25 animals with burns received twice a day on one side of the neck an ointment of a 2% carboxymethylcellulose gel (Whatman) containing 2% polypropyleneglycol, 0.3% calcium lactate, 0.2% propylparaben and 25 ng/ml gel of pure polypeptide of the invention. On the other side of the neck the animals received the same gel but without the polypeptide. The healing time of the wounds on both sides was examined every second day.

In a different set of experiments 15 animals with punch wounds and 15 animals with burn wounds were treated with the gel as described above. At day 5, 10 and 20 10 µCi of $^{14}C$-leucine and 10 µCi of $^3H$-thymidine in 20 µl of water was injected into the center of each wound. Five hours later the animals were killed and the skin of the wound area was excised, homogenated in 2 ml of 10% trichloroacetic acid and the precipitated tissue was collected by centrifugation for 10 minutes at 10,000×g. The tissue was examined gravimetrically and the radioactivity determined by liquid scintillation counting in a Packard scintillation spectrometer. The results are given in Table III.

TABLE III

| (A) Healing periods of punch and burn wounds on guinea pigs | | |
|---|---|---|
| | Treatment | |
| | Polypeptide | Placebo |
| Punch wounds | 21 ± 3 days | 28 ± 4 days |
| Burn wounds | 24 ± 3 days | 35 ± 5 days |

| (B) Incorporation of H—thymidine and $^{14}C$—leucine into dried tissue | | | | |
|---|---|---|---|---|
| | Treatment | | | |
| | Polypeptide | | Placebo | |
| | $^3H$ | $^{14}C$ | $^3H$ | $^{14}C$ |
| Day 5 | | | | |
| Punch wounds | 1689 ± 61 | 2142 ± 58 | 972 ± 41 | 1320 ± 45 |
| Burn wounds | 1423 ± 53 | 1923 ± 42 | 854 ± 32 | 1130 ± 33 |
| Day 10 | | | | |
| Punch wounds | 1034 ± 51 | 1052 ± 31 | 913 ± 34 | 1184 ± 54 |
| Burn wounds | 918 ± 44 | 913 ± 23 | 803 ± 40 | 992 ± 38 |

Treatment of the wounds with an ointment containing 25 nanogram/ml of pure polypeptide from beef plasma resulted in a healing time reduction of 25–30%. Ointments containing 100 ng/ml of pure polypeptide from beef plasma resulted in a healing time reduction of 25–35%. The incorporation tests with $^{14}C$-leucine and with $^3H$-thymidine showed that the proliferation of epithelium cells and fibroblasts was accelerated in the early phase of healing. At day 10 and 20 (not shown) almost no differences of thymidine and leucine incorporation was found between placebo and polypeptide.

(c) Properties of the Polypeptide From Beef Plasma

The polypeptide isolated above is heat resistant, but sensitive to proteases. Trypsin cleavage resulted in a complete loss of biological activity. Trypsin cleavage occurred with 10 µg of the polypeptide of the invention and 1 µg of trypsin in 1 ml of a 10 mM borate buffer at pH 8,2. The CM-cellulose column fraction is a singular, homogeneous polypeptide as determined in two-dimensional polyacrylamide gel electrophoresis. (First dimension: Isoelectrofocusing in 5% polyacrylamide with a linear ampholine gradient (pH 4–10) in the presence of 8M urea. Second dimension: Migration in a 10–25% polyacrylamide gel gradient in the presence of 0.1% SDS). In this system the protein was determined to have an isoelectric point of 8.3 and a molecular weight of 5700–6000. Its molecular weight is 5800 as determined by gel filtration on Sephadex G50 (Pharmacia) in the presence of 8M urea and calibrating proteins and it consists of 52 amino acids according to amino acid analysis in a Beckman automatic amino acid analyzes. For amino acid analysis aliquots of the pure polypeptide were hydrolyzed in 6M HCl at 110° C. for 12, 18 and 24 hours. The nearest integer of the amino acids after amino acid analysis is given in Table IV.

TABLE IV

| Amino acid compositon of the polypeptide | |
|---|---|
| Alanine 4 | Lysine 3 |
| Arginine 4 | Methionine 1 |
| Asparagine 3 | Phenyl alanine 4 |
| Cysteine 4 | Proline 4 |
| Glutamine 5 | Serine 4 |
| Glycine 5 | Threonine 2 |
| Histidine 1 | Tryptophane 0 |
| Isoleucine 1 | Tyrosine 2 |
| Leucine 3 | Valine 2 |

EXAMPLE 2

(a) Isolation of the Glycosteroid and the Glycosphingolipid

The glycosteroid and the glycosphingolipid of the invention were isolated in concentrated form from beef heart according to the biochemical parting procedures described below.

25 kg of beef heart were homogenized mechanically in the presence of 50 l of 0.2% NaCl solution at 4° C. Cellular debris was removed by centrifugation for 15 minutes at 10000×g. The clear supernatant was ultrafiltered at 4° C. through dialysis tubes or ultrafilter membranes having an exclusion limit for molecules having a molecular weight greater than 10,000.

The ultrafiltrate was concentrated under vacuum at 40° C. until the ionic strength of the solution corresponded to that of a physiological common salt solution (i.e. 0.8% NaCl). The organic material in the solution was bound to active carbon by suspending 200 g active carbon in the ultrafiltrate. The active carbon was centrifuged off after agitation with the solution for 30 minutes. Thereupon the active carbon was extracted with 100 ml 10% acetic acid or propionic acid. The solvent of the extract was removed under vacuum at 40° C. and the residue was taken up in 100 ml 1M acetic acid.

The resulting acid solution was chromatographed over a molecular sieve, i.e., a 10-liter Biogel P 20 column (Biorad). A small percentage of the polypeptide of the invention eluted from the column after 1/6 of a column volume of eluate. In blood this is normally globulin-associated and therefore is retained by the filter membrane. After 1 column volume of eluate, the glycosphingolipid eluted. After 1.7 column volume the glycosteroid eluted. The solvents of the eluates of the steroid and lipid were removed under vacuum at 40° C.

The lipid portion was dissolved in a small volume of 0.1% acetic acid and charged on a silica gel absorption/desorption column covered with C-8 chains and equilibrated with 0.1% acetic acid. The column was then washed with a logarithmic gradient of 0.1% acetic acid to 90% ethanol. The lipid eluted with the 30% ethanol containing fraction.

The glycosteroid was taken up in ethanol-methylene chloride (8:1, v/v) and chromatographed over a silica gel column in the same solvent. Three fractions eluted from the column with R$_f$ values of 0.4 (Fraction 1, 80% by weight) 0.55 (Fraction 2, 10% by weight) and 0.7 (Fraction 3, 10% by weight).

The concentrations of the steroid and lipid are shown in Table V.

TABLE V

| | Amount | Purification |
|---|---|---|
| 1. Glycosteroid from Beef Heart | | |
| Dry weight of the ultrafiltrate | 200 mg/ml | |
| Dry weight after silica gel column (sum of Fractions 1–3, calculated on the original volume of the ultrafiltrate) | 1 μg/ml | 200,000× |
| 2. Glycosphingolipid from Beef Heart | | |
| Dry weight of the ultrafiltrate | 200 mg/ml | |
| Dry weight after C-8 silica gel column (calculated on the original volume of the ultrafiltrate) | 5 μg/ml | 40,000× |

The glycosteroid and glycosphingolipid of the invention were purified exactly by the same procedure as described above when lung, muscle or spleen were the source materials. In case of blood, plasma or serum, the fluid was ultrafiltered directly and then processed as described above. Based on the amount of protein in the starting material, the recovery of the glyco-compounds of the invention was 5–8 times higher in beef heart than in beef blood. The recoveries of the glyco-compounds from animal heart was of the same order of magnitude as from animal lung, muscle and spleen. The recoveries of the glyco-compounds from human, swine, horses and sheep were of the same order of magnitude as from beef.

(b) Biological Activity of Glycosteroid and Glycosphingolipid

In vitro the cell-proliferating activity of the glycosphingolipid was tested on primary human fibroblasts and epithelium cells damaged with THO (tritium water) for 24 hours. $^{14}$C-leucine incorporation in protein and $^3$H-thymidine incorporation in DNA was measured in the presence of whole medium (Eagles Medium) and 10 to 50 μg/ml medium of the lipid using a five-hour pulse. $3 \times 10^6$ cells were present in each Petri dish of 5 cm diameter. The concentration of leucine and thymidine was 20 μM. The radioactivity was 1 μCi/ml medium. Controls were treated similarly except for the absence of the lipid in the culture. Cell-proliferation data is compiled in Table VI.

TABLE VI

| | Counts/minute |
|---|---|
| Control | 15,300 |
| Glycosphingolipid | |
| 10 μg/ml | 28,731 |
| 20 μg/ml | 42,310 |
| 50 μg/ml | 71,430 |

In addition to increased $^3$H-thymidine incorporation it was observed that the THO-damaged fibroblasts and epithelium cells began to morphologically resemble normal fibroblasts and epithelium cells after 4 days action with as little as 5 μg/ml of the glycosphingolipid. The glycosteroid from the silica gel was not active in vitro.

In vivo the cell-proliferating activities of both the steroid and the lipid were evidenced by the accelerated healing of punch and burn wounds on guinea pigs as described in Example 1. A continuous treatment of punch and burn wounds on guinea pigs with an ointment containing 5 μg/ml of the glycosphingolipid or 1 μg/ml of the glycosteroid (fraction 1) resulted in a reduction of the healing time by 20%. An ointment containing 50 μg/ml of glyco-sphingolipid or 10 μg/ml of the glycosteroid resulted n a reduction of healing time by 25-30%. For optimal results the ointments consisted of 2% carboxymethyl cellulose (Whatman), 2% propylene-glycol, 0.3% calcium lactate, 0.2% propylparaben and $5 \times 10^{-4}$% each of a mixture of lysine, glutamine, 2-purine and 2-pyrimidine nucleosides (cytidine, guanosine, adenosine and uridine).

Similar results were obtained when the carriers were water-in-oil or oil-in-water emulsions instead of gel or when the glyco compounds were dissolved in 0.8% NaCl-solution and applied to the wounds by aerosol spraying. The carriers alone without the glyco-compounds were not active in the wound healing experiments.

$^{14}$C-leucine and $^3$H-thymidine incorporation tests in vivo were carried out as described for the polypeptide in Example 1 and indicated that the glycospingolipid promoted proliferation of fibroblasts and epithelial cells in the middle and end phase of healing while the steroid promoted proliferation of fibroblasts and epithelium cells in the final healing phase.

The tissue regenerating properties of the glycosphingolipid were evaluated in double blind clinical trials on 25 humans with internal chronic skin ulcers induced after artery-and vein-plugs, after postphlebitis or ulcus cruris. In the trials two different carboxy-methylcellulose gels were applied to the ulcers. Gel I contained 5 μg/g gel of the glycosphingolipid and gel II contained no active ingredient (placebo). The ulcers of the patients were treated alternating one week with gel I and the following week with gel II. The gels were applied twice a day. The tissue regenerating properties of the lipid were evaluated by planimetrical measurement of the surfaces of the individual ulcers once a week and are summarized in Table VII. The results for the glycosphingolipid were excellent in 13 cases (regression >50%), good in 6 cases (regression between 25% and 50%), weak in 2 cases (regression <25%) and zero in 4 cases.

TABLE VII

| Ulcer | Duration of treatment (weeks) | Percentage global regression of initial surface | Percentage amelioration due to Gel I | Percentage amelioration due to Gel II |
|---|---|---|---|---|
| 1 | 10 | 90.9 | 53.7 | 37.2 |
| 2 | 10 | 98.4 | 83.3 | 15.1 |
| 3 | 9 | 100 (cicatrisation complete) | 53.3 | 46.7 |
| 4 | 10 | 87.6 | 54.1 | 23.5 |
| 5 | 6 | 27.9 | 22.6 | 5.3 |
| 6 | 6 | 31.5 | 26.6 | 4.9 |
| 7 | 2 | aggravation | | |
| 8 | 2 | aggravation | | |
| 9 | 6 | 53.4 | 54.9 | −1.6 |
| 10 | 8 | 77.2 | 33.7 | 43.5 |
| 11 | 8 | 53.4 | 40.2 | 13.2 |
| 12 | 4 | aggravation | | |
| 13 | 4 | aggravation | | |
| 14 | 6 | 45.3 | 11.4 | 33.9 |
| 15 | 6 | 17.5 | 22.9 | −5.4 |
| 16 | 2 | 100 | 80 | 20 |
| 17 | 6 | 10.7 | 19.9 | 9.2 |
| 18 | 6 | 100 | 28.5 | 71.5 |
| 19 | 6 | 36.9 | 45.7 | −8.8 |
| 20 | 6 | 85.4 | 62.2 | 23.2 |
| 21 | 6 | 45.5 | 31.8 | 13.7 |
| 22 | 6 | 44.8 | 30.9 | 13.9 |
| 23 | 6 | 79.2 | 60.4 | 18.8 |
| 24 | 6 | 63.3 | 39.9 | 23.4 |
| 25 | 6 | 55 | 26.8 | 28.2 |

(c) Properties of Glycosteroid and Glycosphingolipid

1. Glycosteroid

The structure of the steroid was evaluated as follows:

Incubation of the steroid (fraction 1 from the silica-gel-column) in the presence of β-glucosidase (Worthington) resulted in separation of three molecules of glucose and two molecules of glucoseamine and complete loss of biological activity. Incubation for 1 hour at 80° C. in 0.1N aqueous HCl of the steroid portion after glucosidase treatment resulted in release of one molecule of malonic acid monoamide from the steroidal backbone leaving a primary alcoholic group on the steroid. Incubation of the steroid with 3-α-hydroxysteroid-dehydrogenase in 10 mM phosphate buffer and 1 mM NAD resulted in an 85% loss of the biological activity of the compound. Infrared and GC-MS analysis of the steroid was carried out after treatment with HCl, glucosidase and the steroid-dehydrogenase. The infrared spectrum was identical to that of pregn-4-ene-11-β,17α,21-triol-3,20-dione with major peaks at wave numbers (cm$^{-1}$): 3500, 3460, 2880, 2720, 1670, 1450, 1230, 1090, 890, 880. λmax.=224 and ε=16300 were identical with pregn-4-ene-u,17,21triol-3,20-dione. The GC-field-adsorption-mass-spectrometry after trimethylsilylation of the steroid and pregn-4-ene-11-β,17α,21-triol-3,20-dione showed identical splitting of the molecules with a molecule peak of 578. From the physical-chemical analysis the following structure could be determined:

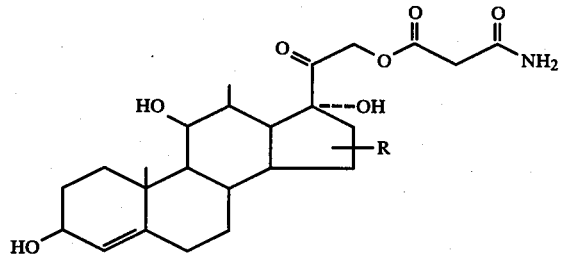

Fractions 2 and 3 showed the same characteristics as described above except that one molecule of acetic acid for fraction 2 and two molecules of acetic acid for fraction 3 were released after HCl treatment.

2. Glycosphingolipid

The structure of the lipid was determined as follows:

Incubation of the lipid in the presence of glycosidase or milk alkaline hydrolysis with sodium methylate resulted in the complete inactivation of its bioligical activity. The residual skeleton of the lipid was determined to be a ceramide by TLC and specific staining methods. Anhydrous methanolysis in the presence of HCl (amide cleavage) followed by coupled GC-MS spectrometry indicated presence of a fatty acid residue having the structure R$_2$=CH$_3$—(CH$_2$)$_9$—CH=CH—CH$_2$— and sphingosin. Incubation of the lipid in the presence of OsO$_4$ produced an oligosaccharide and ceramide. The ceramide was then treated with periodate. Coupled GC-MS spectrometry resulted in the identification of a fatty acid residue with the following structure R$_1$=CH$_3$—(CH$_2$)$_{13}$—CH$_2$—. When the oligosaccharide, which was separated from ceramide, was treated by mild periodate oxidation, 5 sugar residues could be identified: uronic acid, fucose and 3 modified and substituted hexoses.

Based on the above analytical procedures, the structure of the lipid was concluded to be:

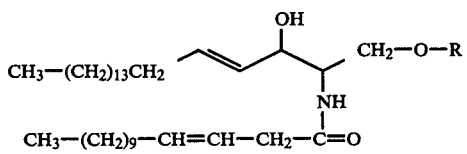

That is, the lipid was determined to be a glycosphingolipid.

Spectrometric Data:

The fatty acid residue ($R_1$) after periodate cleavage was methylated in the presence of a methanolic HCl solution and analyzed by coupled GC-field adsorption mass spectrometry.

The following m/e peaks were obtained:

270 representing the molecule peak (M)

M-31 for $CH_2=\overset{+}{O}H$

M-74 for $H_2C=\underset{OH}{\overset{|}{C}}-OCH_3^+$ and the typical $[C_nH_{2n-1}]^+$-series of 29, 43, 57, 71, 85, 99, 113, 127, 141, 155 and 169.

The fatty acid residue ($R_2$) after methanolic amide cleavage (fatty acid methylester) was incubated in the presence of periodate followed by subsequent hydrolysis with aqueous HCl. Two carboxylic acids were identified by gas chromatography using reference carboxylic acids in parallel runs: HOOC—$CH_2$—COOH and $CH_3$—$(CH_2)_9$—COOH. After GC-field adsorption mass spectrometry both acids gave identical fragmentation when compared with the corresponding reference carboxylic acid. When the $R_2$-methylester was analyzed by coupled GC-field adsorption mass spectrometry the following peaks were obtained:

240 for M

M-31 and M-74 for methoxy radicals and again a typical $[C_2H_{2n-1}]$ series.

We claim:

1. A composition for stimulating wound healing by promoting proliferation of epithelium cells in the final phase of wound healing comprising 1 to 10 μg of a glycosteroid isolated from a protein-free fraction of mammalian tissue or fluid in a pharmaceutically acceptable carrier, said glycosteroid having the structure:

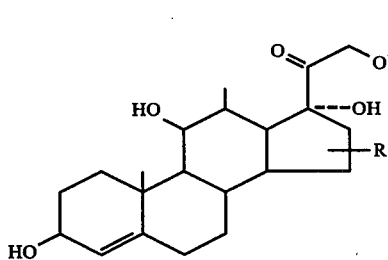

wherein R is an oligosaccharide containing five sugar units wherein the glycosteroid is isolated from mammalian tissue or fluid by:

(a) homogenizing the mammalian tissue or fluid with an aqueous solution of 0.2% NaCl;

(b) clearing the homogenate from the cellular debris by centrifugation or filtration;

(c) thereafter ultra-filtering the cleared homogenate;

(d) concentrating the ultrafiltrate at 40° C. until the ionic strength thereof corresponds to a 0.8% NaCl solution;

(e) binding orgnic material in the concentrated ultrafiltrate to active carbon;

(f) thereafter extracting the active carbon with 10-30% acetic acid;

(g) evaporating the solvent from the extract;

(h) dissolving the residue in 0.2-2M acetic acid;

(i) chromatographing the resulting solution over a molecular sieve column;

(j) thereafter eluting the column with 0.2-2M acetic acid and collecting the second fraction with cell proliferating activity; and (k) removing the solvent from the collected eluate.

2. A method of promoting proliferation of epithelium cells during wound healing comprising treating wound in the final phase of healing with the composition of claim 1.

3. The composition of claim 1 wherein the carrier is selected from the group consisting of carboxymethylcellulose, oil-in-water emulsions, water-in-oil emulsions and aqueous solutions.

4. The composition of claim 1 wherein the glycosteroid is isolated from a mammalian tissue selected from the group consisting of heart, lung, muscle and spleen.

5. The composition of claim 1 wherein the glycosteroid is isolated from a mammalian fluid selected from the group consisting of blood, plasma and serum.

6. The composition of claim 1 wherein the glycosteroid is isolated from the fluid or organ of a mammal selected from the group consisting of human, swine, horses, sheep and beef.

7. The composition of claim 1 wherein the glycosteroid is further concentrated by:

(a) dissolving the dried eluate resulting from step (k) of claim 1 in ethanol-methylene chloride;

(b) chromatographing the dissolved eluate over a silica gel column;

(c) collecting the fractions of silica gel column eluate which have $R_f$ values of 0.4, 0.55 and 0.7; and (d) evaporating the solvent.

8. A composition for promoting fibroblast formation in wounds after capillarization and vascularization begins comprising 5 to 50 micrograms per milliliter of a glycosphingolipid isolated from a protein-free fraction of mammalian tissue or fluid in a pharmaceutically acceptable carrier, said glycosphingolipid having the formula:

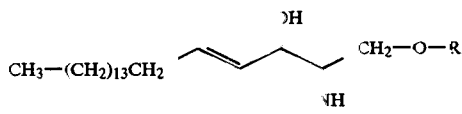

wherein R is an oligosaccharide containing 5 sugar units consisting of uronic acid, fucose and 3 modified and substituted hexoses.

9. A method of promoting fibroblast formation in wounds comprising treating a wound in which vascularization and capillarization has begun with the composition of claim 8.

10. The method of claim 9 wherein the wound is treated with the composition in an amount sufficient to provide 5 to 50μ gram/ml ointment of the glycosphingolipid to the wound.

11. The composition of claim 8 wherein the carrier is selected from the group consisting of carboxymethylcellulose, oil-in-water emulsions, water-in-oil emulsions and aqueous solutions.

12. The composition of claim 8 wherein the glycosphingolipid is isolated from a mammalian tissue selected from the group consisting of heart, lung, muscle and spleen.

13. The composition of claim 8 wherein the glycosphingolipid is isolated from a mammalian fluid selected from the group consisting of blood, plasma and serum.

14. The composition of claim 8 wherein the glycosphingolipid is isolated from the fluid or organ of a mammal selected from the group consisting of humans, swine, horses, sheep and beef.

15. The composition of claim 8 wherein the glycosphingolipid is isolated from mammalian tissue or fluid by:
  (a) homogenizing the mammalian tissue or fluid with an aqueous solution with 0.2% NaCl;
  (b) clearing the homogenate from cellular debris by centrifugation or filtration;
  (c) thereafter ultra-filtering the cleared homogenate;
  (d) concentrating the ultrafiltrate at 40° C. until the ionic strength thereof correspond to a 0.8% NaCl solution;
  (e) binding organic material in the concentrated ultrafiltrate to active carbon (1% by weight)
  (f) thereafter extracting the active carbon with 10–30% acetic acid;
  (g) evaporating the solvent from the extract;
  (h) dissolving the residue in 0.2–2M acetic acid;
  (i) chromatographing the resulting solution over a molecular sieve column;
  (j) thereafter eluting the column with 0.2–2M acetic acid and collecting the first fraction with cell proliferating activity; and
  (k) removing the solvent from the collected eluate.

16. The composition of claim 15 wherein the glycosphingolipid is further concentrated by:
  (a) dissolving the dried eluate resulting from step (k) of claim 15 in acetic acid;
  (b) adsorbing the dissolved eluate on an equilibrated silica gel column having C-8 chains;
  (c) thereafter washing the column with a logarithmic gradient of 0.1% acetic acid—90% alcohol;
  (d) collecting the 30% alcohol containing fraction; and
  (e) evaporating the solvent.

* * * * *